United States Patent [19]

Scarlett

[11] Patent Number: 5,395,990
[45] Date of Patent: Mar. 7, 1995

[54] PROCESS FOR THE PRODUCTION OF ALCOHOLS AND DIOLS

[75] Inventor: John Scarlett, Spennymoor, England

[73] Assignee: Eastman Chemical Company, Kingsport, Tenn.

[21] Appl. No.: 175,542

[22] Filed: Dec. 30, 1993

[30] Foreign Application Priority Data

Dec. 2, 1993 [GB] United Kingdom ............... 9324753

[51] Int. Cl.$^6$ .................... C07C 29/147; C07C 29/14; C07C 27/04
[52] U.S. Cl. ............................ 568/864; 568/830; 568/831; 568/861; 568/862; 568/880
[58] Field of Search ............... 568/822, 830, 864, 880, 568/861, 862

[56] References Cited

U.S. PATENT DOCUMENTS

| | | | |
|---|---|---|---|
| 2,040,944 | 5/1936 | Lazier | 568/844 |
| 2,079,414 | 5/1937 | Lazier | 568/830 |
| 2,091,800 | 8/1937 | Adkins et al. | 568/864 |
| 2,105,664 | 1/1938 | Lazier | 568/864 |
| 2,137,407 | 11/1938 | Lazier | 568/864 |
| 2,755,317 | 7/1956 | Kassel | 585/654 |
| 2,818,393 | 12/1957 | Lefrancois et al. | 502/100 |

(List continued on next page.)

FOREIGN PATENT DOCUMENTS 143634  6/1985  European Pat. Off. .

(List continued on next page.)

OTHER PUBLICATIONS

Mansour et al., "Sel. Hydrog. of Esters to Alcoh. with a Catal. Obtained Rh$_2$O$_3$, Sn (n—C$_4$H$_9$)$_4$ and SiO$_2$ and Based On Isol. Active Centres", *Angew. Chem. 101*, (1989) No. 3, 360–63.

Wehner & Gustafson, "Catalytic Hydrog. of Esters Over Pd/ZnO", *Journ. of Catalysis*, 135, 420–426 (1992).

Lewin et al., "Fiber Chemistry", pp. 8–9 (1985).

Martyn V. Twigg, "Catalyst Handbook", 2nd Ed., p. 54.

Homer Adkins, "Catal. Hydrog. of Esters to Alcoh.", *Organic Reactions*, vol. 8, Chp. 1, pp. 2–27 (1954).

Freifelder, "Catal. Hydrog. in Org. Synth.", pp. 129–151.

Kirk–Othmer, *Encl. of Chem. Tech.*, 3rd Ed., vol. 1, pp. 733–739.

*Primary Examiner*—Werren B. Lone
*Attorney, Agent, or Firm*—J. Frederick Thomsen; Harry J. Gwinnell

[57] ABSTRACT

A process is described for the production of a hydroxylic compound selected from alcohols and diols by hydrogenation of a hydrogenatable material selected from monoesters of carboxylic acids, monoesters of dicarboxylic acids, diesters of dicarboxylic acids, aldehydes, olefinically unsaturated aldehydes, and mixtures of two or more thereof, which process comprises the steps of:

(a) providing a hydrogenation zone containing a charge of a granular hydrogenation catalyst which has a total surface area of at least about 15 m$^2$/g, a pore size distribution such that more than 50% of the pore volume is provided by pores in the size range less than about 40 nm, and a surface area distribution such that more than 50% of the total surface area is provided by pores in the size range of from about 7 nm to about 40 nm;

(b) supplying to the hydrogenation zone a feed stream of a mixture containing hydrogen and the hydrogenatable material;

(c) maintaining the hydrogenation zone under temperature and pressure conditions which are conducive to effecting hydrogenation of the hydrogenatable material; and (d) recovering from the hydrogenation zone a product stream comprising the hydroxylic compound.

The process is exemplified by the hydrogenation of dimethyl 1,4-cyclohexanedicarboxylate to yield 1,4-cyclohexanedimethanol.

21 Claims, 1 Drawing Sheet

U.S. PATENT DOCUMENTS

| | | | |
|---|---|---|---|
| 2,830,095 | 4/1958 | Nicolaisen | 570/231 |
| 2,884,450 | 4/1959 | Holmquist | 568/880 |
| 2,901,466 | 8/1959 | Kibler et al. | 568/830 |
| 2,917,549 | 12/1959 | Hasek et al. | 568/830 |
| 3,334,149 | 8/1967 | Akin et al. | 568/830 |
| 4,032,458 | 6/1977 | Cooley et al. | 568/830 |
| 4,052,467 | 10/1977 | Mills et al. | 568/880 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/864 |
| 4,751,334 | 6/1988 | Turner et al. | 568/864 |
| 4,837,368 | 6/1989 | Gustafson et al. | 568/881 |
| 4,929,777 | 5/1990 | Irick et al. | 568/864 |
| 4,999,090 | 3/1991 | Tateno et al. | 203/36 |
| 5,030,771 | 7/1991 | Fuhrmann et al. | 568/814 |
| 5,124,435 | 6/1992 | Mori et al. | 528/307 |
| 5,142,067 | 8/1992 | Wegman et al. | 549/326 |
| 5,185,476 | 2/1993 | Gustafson et al. | 568/831 |
| 5,191,091 | 3/1993 | Weyman et al. | 549/326 |

FOREIGN PATENT DOCUMENTS

| | | | |
|---|---|---|---|
| 241760 | 10/1987 | European Pat. Off. | |
| 301853 | 2/1989 | European Pat. Off. | |
| 353990 | 2/1990 | European Pat. Off. | |
| 0353990 | 7/1990 | European Pat. Off. | 568/830 |
| 378756 | 7/1990 | European Pat. Off. | |
| 552463 | 7/1993 | European Pat. Off. | |
| 1276722 | 10/1961 | France | |
| 1144703 | 3/1963 | Germany | |
| 1159925 | 12/1963 | Germany | |
| 2719867 | 11/1978 | Germany | |
| 3843956 | 6/1990 | Germany | |
| 4141199 | 6/1993 | Germany | |
| 988316 | 4/1965 | United Kingdom | |
| 1024318 | 3/1966 | United Kingdom | |
| 1454440 | 11/1976 | United Kingdom | |
| 1464263 | 2/1977 | United Kingdom | |
| 2116552 | 9/1985 | United Kingdom | |
| 2250287 | 6/1992 | United Kingdom | |
| 8203854 | 11/1982 | WIPO | |
| 8603189 | 6/1986 | WIPO | |
| 8607358 | 12/1986 | WIPO | |
| 8800937 | 2/1988 | WIPO | |
| 8900886 | 2/1989 | WIPO | |
| 9008121 | 7/1990 | WIPO | |
| 9101961 | 2/1991 | WIPO | |

PROCESS FOR THE PRODUCTION OF ALCOHOLS AND DIOLS

FIELD OF THE INVENTION

This invention relates to a process for the production of a hydroxylic compound selected from alcohols and diols by hydrogenation of a corresponding hydrogenatable material selected from monoesters of carboxylic acids, monoesters of dicarboxylic acids, diesters of dicarboxylic acids, aldehydes, olefinically unsaturated aldehydes, and mixtures of two or more thereof.

BACKGROUND OF THE INVENTION

It is known to produce alcohols by hydrogenation, or more properly hydrogenolysis, of monoesters of carboxylic acids. The reaction can be summarised as follows:

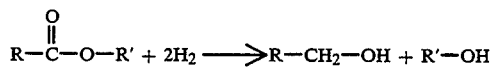
(1)

In the book "Catalytic Hydrogenation" by M. Freifelder, published by John Wiley and Sons Inc. (1978), it is stated at page 129 et seq. that the catalyst of choice is barium promoted copper chromite. In "Organic Reactions", Vol. 8, published by John Wiley and Sons Inc. (1954), Chapter I is by Homer Adkins and is entitled "Catalytic Hydrogenation of Esters to Alcohols". It is suggested that a "copper chromite" catalyst is more correctly described as an approximately equimolar combination of cupric oxide and cupric chromite, i.e. $CuO,CuCr_2O_4$. Reference may also be had to Kirk-Othmer's "Encyclopedia of Chemical Technology" (Third Edition), Volume 1, page 733 to 739.

Patent specifications describing hydrogenation of esters to yield alcohols include U.S. Pat. No. 2,040,944, U.S. Pat. No. 2,079,414, U.S. Pat. No. 2,091,800, and FR-A-1276722.

It is known to effect hydrogenation of certain esters and diesters in the vapour phase. For example it has been proposed to use a reduced copper oxide/zinc oxide catalyst for effecting hydrogenation of esters in the vapour phase. In this connection attention is directed to GB-B-2116552. Also of relevance is WO-A-90/8121.

It is further known to produce diols, such as butane-1,4-diol, by catalytic hydrogenation of esters of dicarboxylic acids, such as a dimethyl or diethyl ester of maleic acid, fumaric acid, succinic acid, or a mixture of two or more thereof. Such processes are described, for example, in GB-A-1454440, GB-A-1464263, DE-A-2719867, U.S. Pat. No. 4,032,458, and U.S. Pat. No. 4,172,961.

Production of butane-1,4-diol by vapour phase hydrogenation of a diester, typically a dialkyl ester, of a $C_4$ dicarboxylic acid selected from maleic acid, fumaric acid, succinic acid, and a mixture of two or more thereof has been proposed. In such a process the diester is conveniently a di-($C_{1-4}$-alkyl) ester, such as dimethyl or diethyl maleate, fumarate, or succinate. A further description of such a process can be found in U.S. Pat. No. 4,584,419, EP-A 0143634, WO-A-86/03189, WO-A-86/07358, and WO-A-88/00937.

Another commercially important diol is 1,4-cyclohexanedimethanol. This compound is used to prepare highly polymeric linear condensation polymers by reaction with terephthalic acid and is useful as an intermediate in the preparation of certain polyester and polyester amides. The use of 1,4-cyclohexanedimethanol for such purposes is disclosed in, for example, U.S. Pat. No. 2,901,466.

One method for preparing 1,4-cyclohexanedimethanol (hexahydroterephthalyl alcohol) involves the hydrogenation of diethyl 1,4-cyclohexanedicarboxylate (diethyl hexahydroterephthalate) in a slurry phase reactor in the presence of a copper chromite catalyst at a pressure of 3000 psia (about 206.84 bar) and a temperature of 255° C., as is described in Example 3 of U.S. Pat. No. 2,105,664. The yield is said to be 77.5%.

The hydrogenation of dimethyl 1,4-cyclohexanedicarboxylate (DMCD) to 1,4-cyclohexanedimethanol (CHDM) is shown below in equation (2):

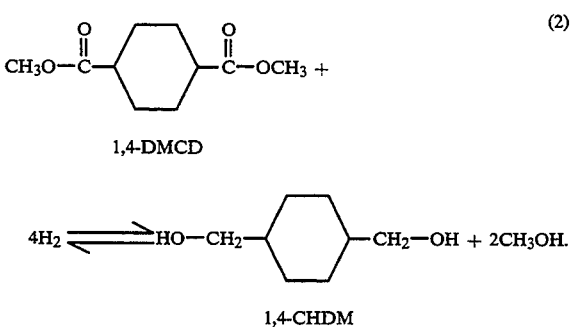

Several processes for the production of 1,4-cyclohexanedimethanol and related alcohols have been published since the issuance of U.S. Pat. No. 2,105,664 in 1938. These processes have, almost exclusively, focused on methods for performing the above hydrogenation reaction in the liquid phase. Advances have been reported in the general areas of cis-/trans- isomer selectivity (U.S. Pat. No. 2,917,549, GB-A-988316 and U.S. Pat. No. 4,999,090), catalyst type (GB-A-988316 and U.S. Pat. No. 3,334,149) and conditions of plant operation (U.S. Pat. No. 5030771).

One problem associated with processes for production of a hydroxylic compound selected from alcohols and diols by hydrogenation of a corresponding hydrogenatable material selected from monoesters of carboxylic acids, monoesters of dicarboxylic acids, diesters of dicarboxylic acids, aldehydes, olefinically unsaturated aldehydes, and mixtures of two or more thereof is the synthesis of unwanted by-products which result, for example, from reactions between one or more of the products with themselves or with the starting material or with an intermediate product. Thus methanol is a product, and dimethyl ether is a by-product, of the hydrogenation of methyl caprate or methyl oleate, and are also to be found among the reaction products when dimethyl maleate is subjected to vapour phase hydrogenation. Further types of by-product observed in hydrogenation of alkyl esters of fatty acids are the alkanes corresponding to the desired alcohols and the ethers formed between the alcohol derived from the acid moiety of the ester and the alkyl alcohol derived from the alkyl moiety of the ester. Particularly when hydrogenating alkyl esters of fatty acid mixtures, e.g. methyl esters of mixed $C_8$ to $C_{18}$ fatty acids, such byproduct alkanes and methyl ethers have boiling points which are close to those of the desired product alcohols. Hence they cannot be readily separated therefrom by conventional methods such as distillation. Moreover the presence of such byproducts in the mixed alcohol products has deleterious effects on the downstream uses thereof, e.g. in detergent production.

In vapour phase hydrogenation of n-butyraldehyde possible by-products include n-butyl butyrate and di-n-butyl ether. Although the ester by-product, n-butyl butyrate, can be hydrogenated to useful product, i.e. n-butanol, di-n-butyl ether is not readily susceptible to hydrogenation and hence is an unwanted by-product. When hydrogenating 2-ethylhex-2-enal potential by-products are 2-ethylhexyl 2-ethylhexanoate and di-(2-ethylhexyl) ether, of which the latter is the more undesirable by-product.

By-product formation is also a problem in the production of 1,4-cyclohexanedimethanol. It can be postulated that the observed by-products are formed by reactions involving feed impurities, methanol contained in a recycle hydrogen stream, and the hydrogenation reaction starting material and product themselves. Hence, for example, GB-A-988316 discusses the minimisation of such by-product make by operating the hydrogenation reaction under "relatively mild conditions" (page 2, lines 55 to 79 of GB-A-988316). By the term "relatively mild conditions" is meant a temperature of at least 200° C., preferably between 240° C. and 300° C. and a pressure of 200 to 300 atmospheres (202.65 bar to 303.98 bar), according to page 2, lines 26 to 32 of GB-A-988316. The problem of unwanted by-products is mentioned in the Examples of U.S. Pat. No. 3,334,149 to the extent that certain by-products are included in the tables of results therein. However, there is no discussion in U.S. Pat. No. 3,334,149 as to how such by-product make could be minimised.

One of the major by-products formed during a hydrogenation reaction producing cyclohexanedimethanol according to equation (2) is the product of the reaction between cyclohexanedimethanol itself and its co-product methanol. If the cyclohexanedimethanol is the 1,4-isomer then the product of this reaction is the mono-methyl ether, formula: 1-hydroxymethyl-4-methoxymethyl-cyclohexane, which has the

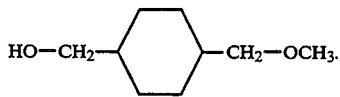

Another by-product which may be formed during production of 1,4-cyclohexanedimethanol is the dimethyl ether, di-(4-hydroxy-methylcyclohexylmethyl) ether, having the formula:

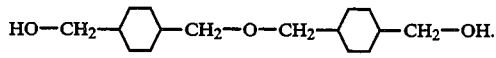

Prior to distillation to effect final purification further by-products can be identified in the crude 1,4-cyclohexanedimethanol product in minor amounts.

The formation of such by-products in the hydrogenation zone results in a loss of the valuable cyclohexanedimethanol product and increases methanol consumption. The presence of by-products in the final cyclohexanedimethanol product requires distillation steps to remove them. The presence of the mono-ether, 1-hydroxy-methyl-4-methoxymethylcyclohexane, in 1,4-cyclohexanedimethanol destined for use in the manufacture of high molecular weight polyesters is desirably avoided since the mono-ether functions as a chain terminator which can result in the formation of an inferior polyester.

In the production of butane-1,4-diol by hydrogenation of a dialkyl maleate typical by-products include gamma-butyrolactone, the corresponding dialkyl succinate, and tetrahydrofuran. Whilst it is possible to hydrogenate both the dialkyl succinate and gamma-butyrolactone to butane-1,4-diol, it is not possible readily to convert tetrahydrofuran to butane-1,4-diol. In some circumstances tetrahydrofuran is itself a valuable product. However, when the primary aim is the production of butane-1,4-diol, tetrahydrofuran can be regarded as an undesirable by-product which serves only to reduce the available yield of butane-1,4-diol. Production of gamma-butyrolactone or dialkyl succinate as a by-product, on the other hand, need not be a disadvantage since either or both of these materials can be recycled to the hydrogenation zone for conversion to the desired product, i.e. butane-1,4-diol.

It is recognised that many of the physical properties required for proper functioning of a catalyst, such as pore diffusion coefficients, are determined by catalyst morphology. Whilst it is not possible to give a complete description of the morphology of a catalyst pellet an approximate definition can be given by reference to average properties such as specific surface area (i.e. total accessible area), specific porosity (i.e. total accessible pore volume), pore size distribution (i.e. distribution of pore volume as a function of pore radius), mean pore radius, and particle size distribution.

In the book "Catalyst Handbook", edited by Martyn V. Twigg, published by Wolfe Publishing Ltd., Second Edition (1989), pores are classified, for example, as macropores (>30–35 nm), micropores (<2 nm), or mesopores (intermediate size). However, these ranges of pore sizes are arbitrary and any other convenient ranges can be used instead to define pore size types.

Whilst it is recognised that the average properties of a catalyst can be used to describe the morphology of a catalyst pellet, it is not possible to predict what effect on the catalyst performance a change in any one of the properties used to describe the morphology will have. Thus it is not possible to predict what effect changes in some or all of the average properties of a catalyst will have on the performance of that catalyst, in particular upon the rate of formation of by-products.

SUMMARY OF THE INVENTION

It is accordingly an object of the present invention to provide a process for the production of alcohols such as n-butanol, 2-ethylhexanol or 2-propylheptanol, or diols, such as cyclohexanedimethanol or butane-1,4-diol, by hydrogenation of a corresponding aldehyde, ester or diester, which significantly reduces the by-product make associated with such a process, relative to the known prior art.

According to the present invention there is provided a process for the production of a hydroxylic compound selected from alcohols and diols by hydrogenation of a hydrogenarable material selected from monoesters of carboxylic acids, monoesters of dicarboxylic acids, diesters of dicarboxylic acids, lactones, aldehydes, olefinically unsaturated aldehydes, and mixtures of two or more thereof, which process comprises the steps of:

(a) providing a hydrogenation zone containing a charge of a granular hydrogenation catalyst which has a total surface area of at least about 15 m$^2$/g, a pore size distribution such that more than 50% of the pore volume is provided by pores in the size range less than about 40 nm, and a surface area distribution such that more than 50% of the total surface area is provided by pores in the size range of from about 7 nm to about 40 nm;

(b) supplying to the hydrogenation zone a feed stream of a mixture containing hydrogen and the hydrogenatable material;

(c) maintaining the hydrogenation zone under temperature and pressure conditions which are conducive to effecting hydrogenation of the hydrogenatable material;

(d) recovering from the hydrogenation zone a product stream comprising the hydroxylic compound.

In preferred catalysts used in the process of the invention less than 50% of the total surface area is provided by pores in the size range of from about 3.7 nm to about 7 nm.

The process of the invention can be operated as a liquid phase process with the feed stream being supplied to the hydrogenation zone in liquid form so that the catalyst bed is essentially wholly wetted with a liquid phase. Normally such liquid phase processes will be associated with use of relatively high pressures, particularly when the material being hydrogenated is an ester or diester. Preferably, however, the process is operated as a vapour phase process in which little or no liquid phase is present on the catalyst surface throughout the catalyst bed or, if the hydroxylic compound is less volatile than the hydrogenatable material, as a partly vapour phase process. In either case the feed stream is supplied to the hydrogenation zone in essentially liquid free vaporous form. Hence the feed stream is supplied in such circumstances to the hydrogenation zone at an inlet temperature which is above the dew point of the mixture. In many cases, particularly when the hydroxylic compound is more volatile than, or is of similar volatility to, the hydrogenarable material, the process will be operated so that vapour phase conditions will exist throughout the hydrogenation zone. If, however, the hydroxylic compound is less volatile than the hydrogenatable material, as is the case when dimethyl 1,4-cyclohexanedicarboxylate is hydrogenated to yield 1,4-cyclohexanedimethanol, there is the possibility of condensation of a hydroxylic compound-rich liquid occurring on the catalyst, particularly if the temperature of the feed stream is close to its dew point. Such condensation of a hydroxylic compound-rich liquid on the catalyst is not deleterious in the process of the invention because the heat of hydrogenation of any hydrogenarable material present in the hydroxylic compound-rich liquid can be dissipated by the heat sink effect of the hydroxylic compound. However, it is essential that the feed stream be at a temperature above its dew point at the inlet end of the catalyst bed if the advantage of vapour phase feed conditions is to be realised. The use of vapour phase feed conditions in the process of the invention has the advantage that, compared with liquid phase operation of the process, generally lower operating pressures can be used. This generally has a significant and beneficial effect not only on the construction costs but also on the operating costs of the plant.

Hence, although the process of the invention can be operated as a liquid phase process, it is preferred to utilise vapour phase feed conditions. In this case the process is operated so that, in step (b), the feed stream is supplied at an inlet temperature which is above the dew point of the mixture. In step (d) the product stream may be recovered in vaporous form at an exit temperature which is above its dew point. Alternatively, particularly if the hydroxylic compound is less volatile than the hydrogenarable material, the product stream may be recovered, in step (d) of the process, as a mixture of liquid and vapour at an exit temperature which is below the dew point of the product stream.

The invention is based upon the surprising discovery that, in the hydrogenation of a hydrogenarable material selected from monoesters of carboxylic acids, monoesters of dicarboxylic acids, diesters of dicarboxylic acids, aldehydes, olefinically unsaturated aldehydes, and mixtures of two or more thereof, the by-product make can be influenced by the pore size distribution of the hydrogenation catalyst used therein.

When the hydrogenarable material is an alkyl or dialkyl ester, for example a $C_1$ to $C_4$ alkyl ester of an aliphatic monocarboxylic acid or a $C_1$ to $C_4$ dialkyl ester of a dicarboxylic acid, the product stream will contain a mixture of the alkyl alcohol, e.g. methanol, and an alcohol or diol derived from the acid moiety of the ester or diester. These hydroxylic materials can react either with themselves or together to yield in each case an ether compound. Thus, for example, when the hydrogenarable material is dimethyl 1,4-cyclohexanedicarboxylate, the products include methanol and 1,4-cyclohexanedimethanol and the by-products include the monoether, 1-hydroxymethyl-4-methoxymethylcyclohexane, as well as the diether, di-(4hydroxymethylcyclohexylmethyl) ether.

For the purposes of the present invention it is convenient to define pore size distribution in terms of a variety of pore size ranges. Although each range is, in itself, rather arbitrary it is helpful nevertheless to make the distinction. For the purposes of the present invention, pore size ranges are defined as follows:

| Pore Size Range | Title |
|---|---|
| About 40 nm to about 7500 nm | super-macro range |
| About 7 nm to about 40 nm | macro range |
| About 3.7 nm to about 7 nm | meso range |
| Less than about 3.7 nm | micro range. |

The values defining the pore size ranges are given in nanometers and refer to the nominal diameter of each pore. In practice, the pores throughout a catalyst will be of irregular cross section and will not generally be uniform in cross section throughout their length.

In general, it is normally considered to be desirable for a catalyst to contain a large quantity of small pores as this will increase the total surface area of the catalyst. However, it has been discovered during the course of the research work which has led to the present invention that, in processes for production of diols, such as cyclohexanedimethanol or butane-1,4-diol, an overabundance of catalyst pore volume provided by pores in the meso range (i.e. about 3.7 nm to about 7 nm) can significantly increase the unwanted by-product make. It has further been discovered that, by choosing a catalyst having more than 50% of its pore volume provided by pores in the macro range, such by-product make can be minimised. Preferred catalysts have at least about 70% up to about 85% or more of their pore volumes provided by pores having diameters in the range of from about 7 nm to about 40 nm. Two catalysts which have identical chemical properties and differ in their physical properties only in that the distribution of their pore sizes is different will produce significantly different product mixtures, with the catalyst having the greater quantity of its pores in the macro pore range (i.e. about 7 nm to about 40 nm) generally exhibiting the more beneficial effects.

The total surface area of a sample of catalyst, which is typically expressed in $m_2/g$, can be measured by an approximation of the well known BET equation as described in ASTM Test Method Designation D 4567-86, entitled "Standard Test Method for Single-Point Determination of Surface Area of Catalysts Using Nitrogen Adsorption by Continuous Flow Method". This method involves degassing the sample of catalyst by heating in a flow of inert gas to remove adsorbed vapours from the surface, followed by immersion of the sample in a liquid nitrogen bath causing adsorption of nitrogen from a flowing mixture of a fixed concentration of nitrogen in helium. When adsorption is complete, the sample is allowed to warm to room temperature causing desorption, which results in an increase in the nitrogen concentration in the flowing mixture. The quantity of nitrogen gas desorbed is determined by sensing the change in thermal conductivity. Preferably, however, the total surface area is measured as described in ASTM Test Method Designation D 3683-92, entitled "Standard Test Method for Surface Area of Catalysts". This describes a method for determining the surface area of a catalyst by measuring the volume of nitrogen gas adsorbed at various low pressure levels by the catalyst sample. Pressure differentials caused by introducing the catalyst surface area to a fixed volume of nitrogen in the test apparatus are measured and used to calculate BET surface area. At least four data points are used.

ASTM Test Method Designation D 4284-92, entitled "Standard Test Method for Determining Pore Volume Distribution of Catalysts by Mercury Intrusion Porosimetry", provides a description of a method by which the pore volume distribution of a catalyst sample can be measured. Typically the pore volume distribution is expressed in $mm^3/g$. In this test the non-wetting liquid mercury is forced into the pores of the catalyst and the volume of the intruded pores is determined by measuring the volume of mercury that is forced into them at various pressures.

From the values obtained for the total surface area of the catalyst and from the pore volume distribution measurements it is then possible to calculate the surface area provided by pores of various size ranges.

The acidity of the catalyst is often of interest since it may affect by-product formation. A suitable method of measuring the acidity of a catalyst is given in ASTM Test Method Designation D 4824-88. This uses a technique in which a sample of the catalyst is degassed by heating in a vacuum to remove adsorbed vapours from the catalyst surface, followed by exposure of the degassed catalyst to an excess of gaseous ammonia in a static volumetric system. The excess ammonia is removed by freezing it into a trap cooled with liquid nitrogen. Measurement of the difference between the volume of ammonia before exposure and the volume recovered in the trap is used to calculate the quantity of chemisorbed ammonia and hence the acidity of the catalyst surface. Typically the acidity is expressed in mmol/g.

Preferred catalysts have total surface areas of at least about 20 $m^2/g$, more preferably at least about 25 $m^2/g$. Especially preferred are catalysts having a total surface area of at least about 35 $m^2/g$, even more preferably at least about 40 $m^2/g$, up to about 55 $m^2/g$ or more. Typical catalysts have total surface areas of at least about 30 $m^2/g$ or more. It is also preferred that at least about 60%, and even more preferably at least about 70% up to about 85% or more of the total surface area of the catalyst is provided by pores in the macro range, i.e. about 7 to about 40 nm, and that no more than about 15% to about 40%, and preferably no more than about 25%, of the total surface area is provided by pores in the meso range, i.e. about 3.7 nm to about 7 nm.

The acidity of the catalyst is preferably as low as possible. Typically it is less than about 0.40 mmol/g , for example less than about 0.20 mmol/g, more preferably less than about 0.15 mmol/g, down to about 0.05 mmol/g or less.

The invention further provides a process for the production of cyclohexanedimethanol which comprises the steps of:

(a) providing a hydrogenation zone containing a charge of a granular hydrogenation catalyst which has a total surface area of at least about 20 $m^2/g$, a pore size distribution such that more than 50% of the pore volume is provided by pores in the size range less than about 40 nm, and a surface area distribution such that more than 50% of the total surface area is provided by pores in the size range of from about 7 nm to about 40 nm;

(b) supplying to the hydrogenation zone a feed stream of a mixture containing hydrogen and dialkyl cyclohexanedicarboxylate;

(c) maintaining the hydrogenation zone at a temperature of from about 150° C. to about 350° C. and a pressure of from about 150 psia (about 10.34 bar) to about 2000 psia (about 137.90 bar); and (d) recovering from the hydrogenation zone a product stream comprising cyclohexanedimethanol. In such a process it is preferred that the cyclohexanedimethanol is 1,4-cyclohexanedimethanol, the dialkyl cyclohexanedicarboxylate is dimethyl 1,4-cyclohexanedicarboxylate, the hydrogenation zone is maintained at a temperature of from about 200° C. to about 260° C. and a pressure of from about 450 psia (about 31.03 bar) to about 1000 psia (about 68.95 bar), and the catalyst is selected from the reduced forms of CuO/ZnO, copper chromite and manganese promoted copper catalysts.

In a preferred process the dialkyl cyclohexanedicarboxylate is a di-($C_1$ to $C_4$ alkyl) cyclohexanedicarboxylate, e.g. a dimethyl, diethyl, di-N- or -iso-propyl, or di-n-, -iso- or -sec-butyl cyclohexanedicarboxylate, more preferably dimethyl cyclohexanedicarboxylate.

Whilst the process is used to advantage for the hydrogenation of dimethyl 1,4-cyclohexanedicarboxylate to produce 1,4-cyclohexanedimethanol, it will be understood by those skilled in the art that the process of the invention may be equally well applied to the hydrogenation of any or all of dimethyl 1,2-cyclohexanedicarboxylate, dimethyl 1,3-cyclohexanedicarboxylate or dimethyl 1,4-cyclohexanedicarboxylate. It can also be applied to the hydrogenation of a dialkyl ester, preferably a di-($C_1$ to $C_4$-alkyl) ester, of a $C_4$ dicarboxylic acid, such as maleic acid, fumaric acid, succinic acid, or a mixture of two or more thereof (e.g. dimethyl or diethyl maleate) for the production of butane-1,4-diol. Lactones containing, for example from 4 to about 16 carbon atoms, such as gamma-butyrolactone or epsiloncaprolactone, can be hydrogenated to the corresponding diols, such as butane-1,4-diol or hexane-1,6-diol, according to the teachings of the invention. The process of the invention can also be used to good effect in the production of alcohols by hydrogenation of aldehydes containing, for example, up to about 30 carbon atoms. Examples of such reactions are the hydrogenation of n-butyraldehyde to n-butanol, of 2-methylpropanal to 2-methylpropanol, of n-valeraldehyde to n-pentanol, of 2-ethylhexen-2-al to 2-ethylhexanol, of 2-propylhept-2-enal to 2-propylheptanol and of 4-methoxycarbonylcyclohexanecarboxaldehyde to 1,4-cyclohexanedimethanol. Similarly benefits can also be expected in the hydrogenation of monoesters of monocarboxylic acids to alcohols, for example in hydrogenation of alkyl esters, e.g. methyl or ethyl esters, of $C_1$ to $C_{22}$ alkylcarboxylic acids. Examples of such reactions include hydrogenation of methyl esters of $C_8$ to $C_{18}$ saturated and unsaturated fatty acids and mixtures thereof. Other hydrogenation reactions yielding diols include hydrogenation of di-($C_1$ to $C_4$ alkyl) esters of glutaric acid, pimelic acid, and azelaic acid.

The process of the invention normally is operated at a feed temperature of at least about 100° C. and no higher than about 350° C. The feed temperature is preferably in the range of from about 150° C. to about 300° C., most preferably about 200° C. to about 260° C.

The feed pressure typically is in the range of from about 150 psia (about 10.34 bar) to about 2000 psia (about 137.90 bar). However, it is preferred that the feed pressure is from about 450 psia (about 31.03 bar) to about 1000 psia (about 68.95 bar).

When operating under vapour phase feed conditions the vaporous feed stream must be above its dew point so that the hydrogenarable material is present in the vapour phase at the inlet end of the or each catalyst bed. This means that the composition of the vaporous feed mixture must be controlled so that, under the selected operating conditions, the temperature of the mixture at the inlet end of the or each catalyst bed is always above its dew point at the operating pressure. By the term "dew point" is meant that temperature at which a mixture of gases and vapours just deposits a fog or film of liquid. This dew point liquid will normally contain all the condensable components of the vapour phase, as well as dissolved gases, in concentrations that satisfy the usual vapour/liquid criteria. Typically the inlet temperature of the vaporous feed mixture to the hydrogenation zone is from about 5° C. up to about 10° C. or more above its dew point at the operating pressure.

A convenient method of forming a vaporous mixture for use in the process of the invention is to spray liquid hydrogenatable material or a solution thereof into a stream of hot hydrogen-containing gas so as to form a saturated or partially saturated vaporous mixture. Alternatively such a vapour mixture can be obtained by bubbling a hot hydrogen-containing gas through a body of the liquid hydrogenarable material or solution thereof. If a saturated vapour mixture is formed it should then be heated further or diluted with more hot gas so as to produce a partially saturated vaporous mixture prior to contact with the catalyst.

In order to maintain the vaporous feed stream above its dew point at the inlet end of the or each catalyst bed at the operating pressure the hydrogen-containing gas:-hydrogenatable material molar ratio is desirably at least about 10:1 up to about 8000:1, preferably in the range of from about 200:1 to about 1000:1. In those cases where the hydroxylic compound is significantly less volatile than the hydrogenarable material it is not, however, necessary that the vaporous mixture in contact with all parts of the or each catalyst bed should be so far above its dew point as to prevent condensation of a hydroxylic compound-rich liquid. For example, 1,4-cyclohexanedimethanol is less volatile than the ester starting material, dimethyl 1,4-cyclohexanedicarboxylate, and in this case the process can be operated so that, although the feed stream is wholly vaporous, some condensation of a 1,4-cyclohexanedimethanol-rich liquid occurs on the catalyst in passage through the catalyst bed.

The hydrogen-containing gas used in the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. For example, in the hydrogenation of a dialkyl (e.g. dimethyl) cyclohexanedicarboxylate using gas recycle, the gas recycle stream will contain minor amounts of an alkanol (e.g. methanol).

Although the process of the invention is operated with the feed stream in the vapour phase, it is convenient to express the feed rate of the hydrogenarable material to the hydrogenation zone as a space velocity and to express that space velocity as a liquid hourly space velocity. Hence it is convenient to express the feed rate in terms of the ratio of the liquid feed rate of the hydrogenarable material to the vaporisation zone to the volume of the hydrogenation catalyst. Thus the equivalent liquid hourly space velocity of the hydrogenarable material through the hydrogenation catalyst is preferably from about 0.05 to about 4.0 $h^{-1}$. In other words it is preferred to feed the liquid hydrogenarable material to the vaporisation zone at a rate which is equivalent to, per unit volume of catalyst, from about 0.05 to about 4.0 unit volumes of unsaturated compound per hour (i.e. about 0.05 to about 4.0 $m^3 h^{-1}$ per $m^3$ of catalyst). Even more preferably the liquid hourly space velocity is from about 0.1 $h^{-1}$ to about 1.0 $h^{-1}$. If the hydrogenarable material is a solid at ambient temperatures, then it may be necessary to heat it sufficiently to melt it or to dissolve it in a suitable inert solvent, in which latter case the solvent is ignored for the purpose of measuring the liquid hourly space velocity.

It will be readily apparent to those skilled in the art that the rate of passage of the vaporous feed stream through the hydrogenation zone will depend upon the feed rate of the hydrogenarable material to the vaporisation zone and upon the hydrogen-containing gas:hydrogenatable material molar ratio.

When using dimethyl 1,4-cyclohexanedicarboxylate feed there may be used any feedstock containing a significant quantity of dimethyl 1,4-cyclohexanedicarboxylate. The feed ester dimethyl 1,4-cyclohexanedicarboxylate is commercially available as high purity dimethyl 1,4-cyclohexanedicarboxylate, technical grade dimethyl 1,4-cyclohexanedicarboxylate, cis-dimethyl 1,4-cyclohexanedicarboxylate, or trans-dimethyl 1,4-cyclohexanedicarboxylate. The preferred feedstock for the process of the invention is the technical grade dimethyl 1,4-cyclohexanedicarboxylate, as the high purity, cis-dimethyl 1,4-cyclohexanedicarboxylate, and trans-dimethyl 1,4-cyclohexanedicarboxylate will have required additional purification stages to produce these grades.

The granular catalyst used in the process of the invention may be any catalyst capable of catalysing hydrogenation or hydrogenolysis of an ester, lactone or aldehyde to corresponding alcohol(s) or diol(s). It may be formed into any suitable shape, e.g. pellets, rings or saddles.

Typical ester hydrogenation catalysts include copper-containing catalysts and Group VIII metal-containing catalysts. Examples of suitable copper-containing catalysts include copper-on-alumina catalysts, reduced copper oxide/zinc oxide catalysts, with or without a promoter, manganese promoted copper catalysts, and reduced copper chromite catalysts, with or without a promoter, while suitable Group VIII metal-containing catalysts include platinum catalysts and palladium catalysts. Suitable copper oxide/zinc oxide catalyst precursors include CuO/ZnO mixtures wherein the Cu:Zn weight ratio ranges from about 0.4:1 to about 2:1. An example is the catalyst precursor bearing the designation DRD 92/71. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor available under the designation DRD 92/92. Suitable copper chromite catalyst precursors include those wherein the Cu:Cr weight ratio ranges from about 0.1:1 to about 4:1, preferably from about 0.5:1 to about 4:1. Catalyst precursors of this type are the precursors available under the designation DRD 89/21 or under the designation PG 85/1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89.

All of the above mentioned catalysts available under the general designations DRD or PG can be obtained from Davy Research and Development Limited, P.O. Box 37, Bowesfield Lane, Stockton-on-Tees, Cleveland TS18 3HA, England.

Other catalysts which can be considered for use include Pd/ZnO catalysts of the type mentioned by P. S. Wehner and B. L. Gustafson in Journal of Catalysis 136, 420–426 (1992), supported palladium/zinc catalysts of the type disclosed in U.S. Pat. No. 4,837,368 and U.S. Pat. No. 5,185,476, and chemically mixed copper-titanium oxides of the type disclosed in U.S. Pat. No. 4,929,777.

Further catalysts of interest for use in the process of the invention include the rhodium/tin catalysts reported in A. El Mansour, J. P. Candy, J. P. Bournonville, O. A. Ferrehi, and J. M. Basset, Angew. Chem. 101, 360 (1989).

Any recognised supporting medium may be used to provide physical support for the catalyst used in the process of the invention. This support can be provided by materials such as zinc oxide, alumina, silica, alumina-silica, silicon carbide, zirconia, titania, or any suitable combination thereof.

The catalysts that are particularly preferred for use in the process of the invention are the copper-containing catalysts, particularly the reduced forms of copper chromite, promoted copper chromite, and manganese promoted copper catalyst precursors described hereinabove.

When hydrogenating an aldehyde, such as n-butyraldehyde or 2-ethylhex-2-enal, to a corresponding alcohol, such as n-butanol or 2-ethylhexanol, there may be used any suitable aldehyde hydrogenation catalyst, for example, a reduced CuO/ZnO mixture, a reduced copper chromite, a reduced promoted copper chromite, or a reduced manganese promoted copper catalyst.

Although the process of the invention can be carried out using a single catalyst bed, it is also contemplated to use a hydrogenation zone which comprises two or more hydrogenation reactors connected in series.

The or each hydrogenation zone may comprise a shell-and-tube reactor which may be operated under isothermal, or near isothermal, conditions with the catalyst in the tubes and the coolant in the shell or vice versa. Usually, however, it will be preferred to use adiabatic reactors since these are cheaper to construct and install than shell-and-tube reactors. Such an adiabatic reactor may contain a single charge of a hydrogenation catalyst or may contain two or more beds of catalyst, or beds of different hydrogenation catalysts. If desired, external or internal inter-bed heat exchangers may be provided in order to adjust the inlet temperature to one or more beds of catalyst downstream from the inlet to the adiabatic hydrogenation reactor.

DETAILED DESCRIPTION OF THE PREFERRED EMBODIMENTS

Figure 1:
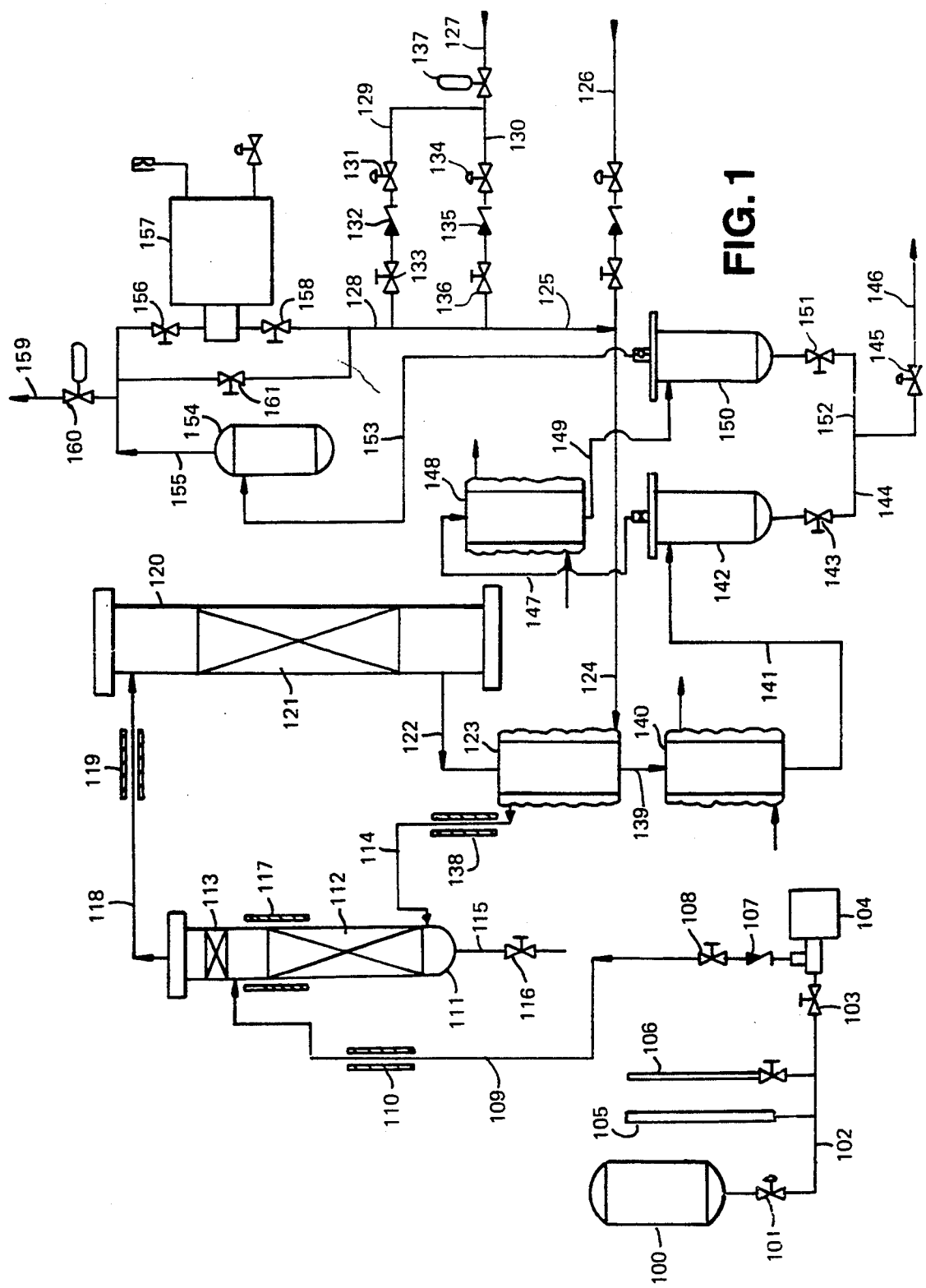
FIG. 1 is a simplified flow diagram of an experimental apparatus for production of a hydroxylic compound, such as 1,4-cyclohexanedimethanol, in a single hydrogenation zone by hydrogenation of an appropriate hydrogenarable material, such as dimethyl 1,4-cyclohexanedicarboxylate.

The invention is further described with reference to the following Examples. The compositions and physical properties of catalysts A and B used in the Examples are listed in Table I.

TABLE I

| Catalyst | Composition wt % | | | Acidity mmol/g | Surface area m²/g | Density g/cm³ | Pore volume mm³/g (%) | | | Surface area distribution m²/g (%) | | |
|---|---|---|---|---|---|---|---|---|---|---|---|---|
| | Cu | Mn | Al | | | | Super-macro | Macro | Meso | Super-macro | Macro | Meso |
| A DRD 92/89 Type A | 41.1 | 6.2 | 20.4 | 0.11 | 47 | 1.452 | 3.6 (1.72) | 186 (89.04) | 19.3 (9.24) | 0.131 (0.28) | 38.24 (81.41) | 8.6 (18.31) |
| B DRD 92/89 Type B | 42.3 | 6.8 | 19.7 | 0.10 | 50 | 1.452 | 17.0 (8.57) | 115.7 (58.35) | 65.6 (33.08) | 0.70 (1.4) | 14.96 (29.92) | 34.34 (60.68) |

Notes:-
1. Super-macro = 40 nm to 7500 nm
2. Macro = 7 nm to 40 nm
3. Meso = 3.7 nm to 7 nm

Examples 1 and 2

The hydrogenation of a high purity grade of dimethyl 1,4-cyclohexanedicarboxylate was investigated using the experimental apparatus illustrated in FIG. 1.

The composition of the high purity feed was: 36.16 wt % trans-dimethyl 1,4-cyclohexanedicarboxylate, 63.26 wt % cis-dimethyl 1,4-cyclohexanedicarboxylate, 0.17% methyl hydrogen 1,4-cyclohexanedicarboxylate of formula

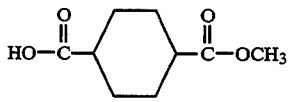

and 0.07 wt % water, with the balance being impurities.

In a commercial plant, hydrogen gas is separated from the hydrogenation product and is advantageously recycled through the hydrogenation zone. The hydrogen recycle stream will contain a quantity of methanol vapour produced by the hydrogenation of dimethyl 1,4-cyclohexanedicarboxylate. Hence, the vaporous mixture supplied to the hydrogenation zone in a commercial plant will generally contain methanol in addition to hydrogen and an unsaturated organic compound. In order that the experimental rig described hereinbelow should accurately predict the likely results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described hereinbelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In this Example and in all succeeding Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 1. An approximately 70 wt % solution of the high purity grade of dimethyl 1,4-cyclohexanedicarboxylate in methanol is fed from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6mm×6mm glass rings 112. A stainless steel demister pad 113 is fitted at the top end of the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 300 ml (428.1 g) of a pelleted manganese promoted copper on alumina hydrogenation catalyst 121. The catalyst is catalyst A of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) wrapped around reactor 120 under the control of appropriately positioned thermocouples (not shown) and by thermal insulation of the reactor 120. The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and control valve 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of catalyst was placed in reactor 120 which was then purged with nitrogen. The catalyst charge was then reduced carefully by a method similar to that described in EP-A-0301853.

High purity dimethyl 1,4-cyclohexanedicarboxylate, appropriately diluted with methanol, was then pumped to the vaporiser 111 at a rate of 126 ml/h corresponding to a liquid hourly space velocity of 0.42 h$^{-1}$. The hydrogen-containing gas:dimethyl 1,4-cyclohexanedicarboxylate molar ratio in the vaporous mixture in line 118 was 703:1. The reactor 120 was maintained at a temperature of 220° C. and a pressure of 900 psia (62.05 bar).

The hydrogenation zone was therefore operated under conditions which prevented the condensation of both dimethyl 1,4-cyclohexanedicarboxylate and the less volatile 1,4-cyclohexanedimethanol product. The temperature throughout the hydrogenation zone was above the dew point at the operating pressure.

The liquid in line 146 was analysed periodically by capillary gas chromatography using a 15 m long, 0.32 mm internal diameter fused silica column coated internally with a 0.25 μm film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. Included amongst the compounds detected in the reaction mixture were 1,4-cyclohexanedimethanol, dimethyl 1,4-cyclohexanedicarboxylate, 4-methoxymethyl cyclohexanemethanol, di-(4-methoxymethylcyclohexylmethyl) ether, and methanol. From the results obtained it appeared that in Example 1 dimethyl 1,4-cyclohexanedicarboxylate had been converted to an extent of 99.90 mol %, with a selectivity to 1,4-cyclohexanedimethanol of 99.13% being obtained, the balance being minor by-products. In Example 2 the conversion of 1,4-dimethyl cyclohexanedicarboxylate was 99.92 mol % with a selectivity to 1,4-cyclohexanedimethanol of 99.46%. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction. The results are listed in Table II below, together with the results from the succeeding Examples 3 to 8.

TABLE II

| Example No. | Pressure psia (bar) | Temp °C. | Gas:DMCD mol ratio | LHSV h$^{-1}$ | DMCD conversion mol % | Selectivity mol % | | | |
|---|---|---|---|---|---|---|---|---|---|
| | | | | | | CHDM | BYPR | METH | DETH |
| 1 | 900 (62.05) | 220 | 703 | 0.42 | 99.90 | 99.13 | 0.57 | 0.11 | 0.19 |
| 2 | 900 (62.05) | 220 | 696 | 0.40 | 99.92 | 99.46 | 0.35 | 0.09 | 0.10 |
| 3 | 901 (62.12) | 219 | 726 | 0.49 | 99.66 | 99.46 | 0.37 | 0.07 | 0.10 |
| 4 | 900 (62.05) | 220 | 704 | 0.51 | 99.49 | 99.54 | 0.30 | 0.08 | 0.08 |
| 5 | 900 (62.05) | 220 | 685 | 0.62 | 98.73 | 99.43 | 0.36 | 0.06 | 0.15 |
| 6 | 900 (62.05) | 220 | 683 | 0.62 | 99.80 | 99.48 | 0.31 | 0.07 | 0.14 |
| 7 | 899 (61.98) | 220 | 676 | 0.41 | 99.69 | 96.99 | 0.89 | 1.45 | 0.67 |
| 8 | 899 (61.98) | 220 | 382 | 0.43 | 99.79 | 98.11 | 1.09 | 0.67 | 0.13 |

Notes to Table II:
DMCD = dimethyl 1,4-cyclohexanedicarboxylate
LHSV = liquid hourly space velocity
CHDM = cyclohexanedimethanol
BYPR = miscellaneous byproducts
METH = 4-methoxymethyl cyclohexanemethanol
DETH = di-(4-hydroxymethylcyclohexylmethyl) ether
Gas = hydrogen-containing gas containing more than 98% v/v hydrogen

EXAMPLES 3 to 6

The high purity dimethyl 1,4-cyclohexanedicarboxylate supplied to the hydrogenation zone in Examples 1 and 2 was replaced with a technical grade feed. The composition of the technical grade feed was: 33.95 wt % trans-dimethyl 1,4-cyclohexanedicarboxylate, 61.60 wt % cis-dimethyl 1,4-cyclohexanedicarboxylate, 1.59 wt % methyl hydrogen 1,4-cyclohexanedicarboxylate, 0.07 wt % water and 2.79 wt % of high boiling impurities including di-4-hydroxymethylcyclohexyl methyl ether. The feed was supplemented with methanol as described in Examples 1 and 2. Detailed results are shown in Table II. In each of these Examples the vaporous mixture in contact with the catalyst was above its dew point.

EXAMPLES 7 and 8

(Comparative Examples)

The charge of copper/manganese/alumina catalyst having a pore size distribution within the scope of the invention used in Examples 1 to 6 was replaced by 300 ml of catalyst B of Table I, i.e. DRD 92/89 type B, a catalyst having the same chemical composition as catalyst A, i.e. DRD 92/89 type A. The catalyst (i.e. catalyst B) was activated following the procedure described in Example 1 and technical grade dimethyl 1,4-cyclohexanedicarboxylate was supplied to the vaporiser 111 at a rate of 123 ml/h corresponding to a liquid hourly space velocity of 0.41 $h^{-1}$. The hydrogen-containing gas:ester molar ratio of the vaporous mixture reaching the hydrogenation zone was 676:1 and the hydrogenation zone was maintained at 900 psia (62.05 bar) and 220° C., i.e. above the dew point of the reaction mixture at this pressure.

A conversion of 99.69% dimethyl 1,4-cyclohexanedicarboxylate was obtained but selectivity to 1,4-cyclohexanedimethanol was only 96.99% in Example 7. Detailed results are shown in Table II. Significant by-product formation was observed with levels of 4-methoxymethyl cyclohexanemethanol as high as 1.45 mol % and of di-(4-hydroxymethylcyclohexylmethyl) ether as high as 0.67 mol %. These figures obtained with catalyst B compare unfavourably with the much lower selectivities to 4-methoxymethyl cyclohexanemethanol and di-(4-hydroxymethylcyclohexylmethyl) ether (i.e. 0.06 to 0.11 mol % and 0.08 to 0.19 mol %) observed under similar conditions with catalyst A. Thus catalyst B, whilst nominally of similar composition to that of catalyst A, gives rise to about 20 times more of the undesirable by-product 4-methoxymethyl cyclohexanemethanol and about 8 times more of the equally undesirable by-product di-(4-hydroxymethylcyclohexylmethyl) ether than does catalyst A.

In Example 8, a lower hydrogen-containing gas:ester molar ratio was used but selectivity to 1,4-cyclohexanedimethanol remained low and the yields of the undesirable by-products 4-methoxymethyl cyclohexanemethanol and di-(4-hydroxymethylcyclohexyl-methyl) ether were again much higher with catalyst B than with catalyst A.

EXAMPLES 9 and 10

The procedure of Example 1 is repeated using, in place of dimethyl 1,4-cyclohexanedicarboxylate, dimethyl 1,2-cyclohexanedicarboxylate and dimethyl 1,3-cyclohexanedicarboxylate respectively. Similar results are obtained.

EXAMPLE 11

An experimental rig of the type illustrated in FIG. 1 was packed with 250 ml (377.5 g) of catalyst A. This was reduced carefully according to the same method as described in Examples 1 and 2. Dimethyl maleate was fed from reservoir 100. The initial exit temperature from reactor 120 was 180° C. and the pressure was 900 psia (62.05 bar). The hydrogen-containing gas:dimethyl maleate molar ratio of the vaporous feed mixture to the hydrogenation reactor was 480:1. The dimethyl maleate feed rate corresponded to a liquid hourly space velocity of 0.40 $h^{-1}$. No dimethyl maleate could be detected in the gas chromatogram, indicating that the hydrogenation of dimethyl maleate to dimethyl succinate is rapid and complete. The conversion of dimethyl succinate to products was observed to be 99.0 mol %. Amongst the products, including methanol, tetrahydrofuran, n-butanol, gamma-butyrolactone, dimethyl succinate, butane-1,4-diol, and water, the selectivity to tetrahydrofuran was 2.74 mol % at the beginning of the run, a figure which fell to 0.5 mol % after 500 hours of operation.

EXAMPLE 12

(Comparative Example)

When the catalyst charge of Example 11 was replaced by a similar charge of catalyst B and a similar reduction technique was used, the conversion of dimethyl succinate (the primary hydrogenation product of dimethyl maleate) varied from 96.0 mol % to 98.0 mol %, while the selectivity to tetrahydrofuran was as high as 30 mol % in the initial stage of the run, falling to 10 mol % over the course of 500 hours.

EXAMPLE 13

The procedures of Examples 11 and 12 are repeated using in place of dimethyl maleate one of the following diesters:
 dimethyl fumarate;
 (ii) diethyl maleate;
 (iii) diethyl succinate;,
 (iv) dimethyl succinate;
 (v) dimethyl glutarate;
 (vi) dimethyl adipate;
 (vii) dimethyl pimelate; or
 (viii) dimethyl azelate.
Similar results are observed to those reported for Examples 11 and 12.

EXAMPLE 14

Using catalyst A for the hydrogenation of the following aldehydes:
 (i) n-butyraldehyde;
 (ii) n-valeraldehyde;
 (iii) 2-ethylhex-2-enal;
 (iv) 2-propylhept-2-enal; or
 (v) 4-methoxycarbonylcyclohexylcarboxaldehyde a reduction in formation of by-products is observed compared with catalyst B.

EXAMPLE 15

The general procedure of Examples 1 to 12 is repeated using each of the following esters:
 methyl caprate;
 (ii) methyl oleate;
 (iii) methyl laurate;
 (iv) methyl myristate;
 (v) methyl palmitate;
 (vi) methyl stearate; or
 (vii) a mixture of methyl esters obtained by hydrolysis of coconut oil followed by "topping and tailing" so as to obtain a mixture of fatty acids of defined boiling range.

A reduction in production of by-products is observed when using catalyst A compared with use of catalyst B.

We claim:

1. A process for the production of alcohols and diols by hydrogenation of a hydrogenatable material selected from $C_1$-$C_4$ alkyl monoesters of $C_8$-$C_{18}$ carboxylic acids, $C_1$-$C_4$ alkyl monoesters of $C_4$-$C_9$ dicarboxylic acids, di-$C_1$-$C_4$ alkyl diesters of $C_4$-$C_9$ dicarboxylic acids, lactones selected from gamma-butyrolactone and epsilon-caprolactone, aldehydes containing up to about 30 carbon atoms, 2-ethyl-hexen-2-al, 2-propylhept-2-enal, 4-methoxycarbonylcyclohexylcarboxaldehyde, and mixtures of two or more thereof, which process comprises the steps of:
   (a) providing a hydrogenation zone containing a charge of a granular hydrogenation catalyst which has a total surface area of at least about 15 $m^2$/g, a pore size distribution such that more than 50% of the pore volume is provided by pores in the size range less than about 40 nm, and a surface area distribution such that more than 50% of the total surface area is provided by pores in the size range of from about 7 nm to about 40 nm and wherein the granular hydrogenation catalyst is selected from copper-containing catalysts and Group VIII metal-containing catalysts;
   (b) supplying to the hydrogenation zone a feed stream of a mixture containing hydrogen and the hydrogenatable material;
   (c) maintaining the hydrogenation zone at a temperature in the range of from about 150° C. to about 350° C. and a pressure in the range of from about 150 psia (about 10.34 bar) up to about 2000 psia (about 137.90 bar) to effect hydrogenation of the hydrogenatable material; and
   (d) recovering from the hydrogenation zone a product stream comprising the alcohol or diol.

2. A process according to claim 1, in which in step (b) the feed stream is supplied in vaporous form at a feed temperature which is above the dew point of the mixture.

3. A process according to claim 2, in which in step (d) the product stream is recovered in vaporous form at an exit temperature which is above its dew point.

4. A process according to claim 2, in which in step (d) the product stream is recovered as a mixture of liquid and vapour at an exit temperature below the dew point of the stream.

5. A process according to any one of claim 3, in which the hydrogen-containing gas:hydrogenatable material molar ratio in the vaporous mixture is in the range of from about 200:1 to about 1000:1.

6. A process according to claim 5, in which the hydrogenatable material comprises dimethyl 1,4-cyclohexanedicarboxylate.

7. A process according to claim 5, in which the hydrogenatable material comprises a diester selected from di-$C_1$-$C_4$ alkyl esters of a $C_4$ dicarboxylic acid selected from maleic acid, fumaric acid, succinic acid, and mixtures of two or more thereof.

8. A process according to claim 7, in which the diester comprises dimethyl or diethyl maleate.

9. A process according to claim 5, in which the hydrogenatable material comprises a $C_1$-$C_4$ alkyl monoester of a $C_8$ to $C_{18}$ fatty acid.

10. A process according to claim 5, wherein the hydrogenarable material comprises an aldehyde selected from n-butyraldehyde, n-valeraldehyde, 2-ethyl-hexen-2-al, 2-propylhept-2-enal and 4-methoxycarbonylcyclohexylcarboxaldehyde.

11. A process according to claim 5, in which the feed temperature is in the range of from about 200° C. to about 260° C. and the feed pressure to the hydrogenation zone is in the range of from about 450 psia (about 3103 bar) to about 1000 psia (about 68.95 bar).

12. A process according to claim 5, in which the catalyst is selected from reduced copper oxide/zinc oxide catalysts, reduced manganese promoted copper catalysts, reduced copper chromite catalysts, reduced promoted copper chromite catalysts, platinum catalysts and palladium catalysts.

13. A process according to claim 12, in which the catalyst is selected from reduced manganese promoted copper catalysts, reduced copper chromite catalysts and reduced promoted copper chromite catalysts.

14. A process according to claim 13, in which the catalyst comprises not more than about 15% by weight of at least one promoter selected from barium, manganese, and mixtures thereof.

15. A process according to claim 12, in which the catalyst is at least partially supported on a supporting material selected from zinc oxide, alumina, silica, silica-alumina, silicon carbide, zirconia, titania, or any combination thereof.

16. A process according to claims 5, in which the hydrogenarable material is supplied at a rate corresponding to a liquid hourly space velocity of from about 0.05 to about 4.0 $h^{-1}$.

17. A process according to claim 13, in which the catalyst has a total surface area of at least about 35 $m^2$/g, and at least about 60% of the total surface area of the catalyst is provided by pores in the range of from about 7 to about 40 nm.

18. A process according to claim 17, in which the catalyst has a total surface area of at least about 40 $m^2$/g, and at least about 70% of the total surface area of the catalyst is provided by pores in the range of from about 7 to about 40 nm.

19. A process according to claim 18, in which the catalyst has at least about 70% up to about 85% of its pore volume provided by pores having diameters in the range of from about 7 nm to about 40 nm.

20. A process for the production of cyclohexanedimethanol which comprises the steps of:
   (a) providing a hydrogenation zone containing a charge of a granular hydrogenation catalyst which has a total surface area of at least about 40 $m^2$/g, a pore size distribution such that about 70% up to about 85% of the pore volume is provided by pores in the size range of from about 7 nm to about 40 nm, and a surface area distribution such that about 70% up to about 85% of the total surface area is provided by pores in the size range of from about 7 nm to about 40 nm, wherein not more than about 25% of the total surface area is provided by pores in the size range of about 3.7 nm to about 7 nm and wherein the granular hydrogenation catalyst is selected from reduced copper chromite catalysts wherein the Cu:Cr weight ratio is from about 0.1:1 to about 4:1; reduced, copper chromite catalysts wherein the Cu:Cr weight ratio is from about 0.1:1 to about 4:1 promoted with from about 0.1% by weight up to 15% by weight of barium, manganese or a mixture of barium and manganese; or reduced manganese promoted copper catalysts wherein the Cu:Mn weight ratio is from about 2:1 to about 10:1;

(b) supplying to the hydrogenation zone a feed stream of a mixture containing hydrogen and di-$C_1$-$C_4$ alkyl cyclohexanedicarboxylate;

(c) maintaining the hydrogenation zone at a temperature of from about 150° C. to about 350° C. and a pressure of from about 150 psia (about 10.34 bar) to about 2000 psia (about 137.90 bar); and (d) recovering from the hydrogenation zone a product stream comprising cyclohexanedimethanol.

21. A process according to claim 20, in which the cyclohexanedimethanol is 1,4-cyclohexanedimethanol, the dialkyl cyclohexanedicarboxylate is dimethyl 1,4-cyclohexanedicarboxylate, the hydrogenation zone is maintained at a temperature of from about 200° C. to about 260° C. and a pressure of from about 450 psia (about 31.03 bar) to about 1000 psia (about 68.95 bar).

* * * * *